US00PP09821P

United States Patent [19]

Saville

[11] Patent Number: Plant 9,821

[45] Date of Patent: Mar. 11, 1997

[54] MINIATURE ROSE PLANT NAMED 'SAVASEAT'

[75] Inventor: F. Harmon Saville, Newburyport, Mass.

[73] Assignee: Nor'East Miniature Roses, Inc., Rowley, Mass.

[21] Appl. No.: 601,364

[22] Filed: Feb. 14, 1996

[51] Int. Cl.[6] ..... A01H 5/00

[52] U.S. Cl. ..... Plt./7.1

[58] Field of Search ..... Plt./7.1, 9, 22, Plt./26, 27

[56] References Cited

U.S. PATENT DOCUMENTS

P.P. 8,279 6/1993 McGredy, IV ..... Plt./18
P.P. 8,412 10/1993 Saville ..... Plt./7.1

*Primary Examiner*—Howard J. Locker
*Attorney, Agent, or Firm*—Christie, Parker & Hale, LLP

[57] ABSTRACT

A new miniature rose with pink blend flowers.

1 Drawing Sheet

SUMMARY OF THE INVENTION

The present invention relates to a new and distinct variety of rose plant of the miniature rose class, which was created by crossing as seed parent the variety known as 'Benalav' (U.S. Plant Pat. No. 6,517) and as pollen parent the variety known as 'Macgenev' (U.S. Plant Pat. No. 8,279). The varietal denomination of this new rose is 'Savaseat'.

Among the novel characteristics possessed by this new variety which distinguishes it from its parents and all other varieties of which I am aware is its attractive flowers comprising an unusual blend of yellow, apricot, pink and a mauve shade of pink. A yellow/orange coloration on the petal underside gives the flowers a nearly russet overall appearance in the Spring.

Asexual reproduction by propagation of cuttings of the new variety as performed in Essex County, Mass. shows that the foregoing and other distinguishing characteristics come true to form and are established and transmitted through succeeding propagations.

COMPARISON WITH PARENTS

The seed parent of the new variety produces lavender flowers and the pollen parent produces flowers of mainly apricot coloration.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—'Benalav'.

*Pollen parent.*—'Macgenev'.

Class: Miniature.

The following observations are made of specimens grown under plastic in Essex County, Mass., during August.

FLOWER

Blooming habit: Continuous.

A. Bud:

(1) *Size.*—Small.

(2) *Form.*—Ovate, pointed at tips.

(3) *Color.*—As sepals divide, bud color is near 23D with near 43D at edges.

(4) *Sepals.*—Finely serrated to slightly bearded; about ⅓ longer than the bud before starting to open; lanceolate in shape; roll back to stem with tips curling out as flower matures; rolling upward and outward as hips mature; color near 143C.

(5) *Peduncle.*—Length — about ⅞ inch. Aspect — straight. Strength — erect. Color — near 144B.

B. Bloom:

(1) *Size.*—Average size when fully expanded up to about 2¾ inch.

(2) *Borne.*—Singly and in clusters of 3 to 5 blooms.

(3) *Form.*—Opens rather quickly from high pointed bud to flat open flower; outer edges of ends of petals curl under.

(4) *Petalage.*—Number of petals under normal conditions about 18–20.

(5) *Color.*—During first two days, inner petals at center of flower are a blend of near 55B to 62C, reverse near 24B; outer petals are a blend of near 55B and 62C, reverse near 23C; base of petals at point of attachment near 9B inside and near 8B on reverse; general tonality from a distance shades of pink and apricot; and near russet in the Spring.

(6) *Color change.*—As bloom ages, color changes from near 23D and 43D to near 15D, 27A and near 17D; to near 16D and 37B towards center; to a blend of near 55B and 62C with near 23C; center petals beginning near 10C, outer edges near 38B with some petaloids near 68A changing to center petals of near 11D and edges of near 68D and very tips near 68C; general tonality from a distance shades of apricot and yellow; after three or more days shades of apricot and light pink.

Petals:

(1) *Texture.*—Thick.

(2) *Appearance.*—Inside velvety and outside satiny.

(3) *Form.*—Obovate.

(4) *Arrangement.*—Imbricated, regularly arranged, shingle-like.

(5) *Petaloids in center.*—0–5; may have lighter streak down the center.

(6) *Persistence.*—Drop off cleanly in 4–7 days depending on weather.

(7) *Fragrance.*—Strong, classic rose.

(8) *Lasting quality.*—About 4–7 days on the plant; about 3–6 days as a cut flower.

REPRODUCTIVE ORGANS

A. Stamens, filaments and anthers:

*Arrangement.*—One single row around rim or receptacle just inside petals.

B. Stamens:

*Quantity.*—About 40–50.

C. Filaments:

*Approximate length.*—Varying in length from about 5/32 to about 1/4 inch.

*General color.*—At base near 10B, balance mostly near 48C and near white just below anthers.

D. Anthers:

*Color.*—Near 21B.

E. Pollen

*Color.*—Near 21B.

*Quantity.*—Small amount.

F. Pistils:

*Quantity.*—About 25–30.

G. Styles: Slightly uneven in length to about 5/32 inches long.

*Color.*—Near 53B.

H. Stigmas:

*Color.*—Near 54B.

I. Hips:

*Shape.*—Pear shaped.

*Size.*—Up to about 1/2 to 3/4 inches in diameter.

*Seeds.*—Occasionally one or more seeds protrude.

PLANT

A. Form: Upright and bushy.

B. Growth: Very vigorous, uniform branching.

*Height.*—About 28 inches.

*Spread.*—About 24–30 inches wide.

*Length of flowering stem.*—Varying greatly in length, when borne singly averaging about 6 inches.

C. Foliage: Compound of 3–5 leaflets.

*Size.*—Small.

*Quantity.*—Abundant.

*Color.*—New foliage: Upper side near 137C; under side near 137D flushed with a touch of 184A. Old foliage: Upper side near 137A; under side near 137B.

*Shape.*—Ovate with acute tip.

*Texture.*—Upper side semi-glossy; underside matte.

*Thorns or prickles.*—Very short prickles on some leaf stems.

*Edge.*—Serrated.

*Serration.*—Very fine, uneven.

*Leaf stem.*—Color near 146A; underside mostly near 146C.

*Stipules.*—Very finely serrated; lighter in color than leaf stem; generally up to about 1/2 inch on 3 leaflet leaf; up to about 3/8 inch on 5 leaflet leaf.

*Resistance to diseases.*—Blackspot — Average. Mildew — Average. Rust — Average.

D. Wood:

*New wood.*—Color near 146B; bark smooth.

*Old wood.*—Color near 146A; bark smooth.

E. Thorns:

*Quantity.*—Average in quantity but small in size; very few on laterals from stalk.

*Form.*—Flat base very thin, straight.

*Length.*—Mostly very short; varying in length from about 1/8–5/16 inch.

*Color.*—Near 144B.

*Position.*—Very irregular.

F. Prickles:

*Main stalk.*—None.

*Laterals.*—None.

*Leaves.*—Sometimes very short prickles on leaf stems.

G. Winter hardiness: Needs protection in severe climate.

I claim:

1. A new and distinct variety of rose plant of the miniature rose class, substantially as shown and described.

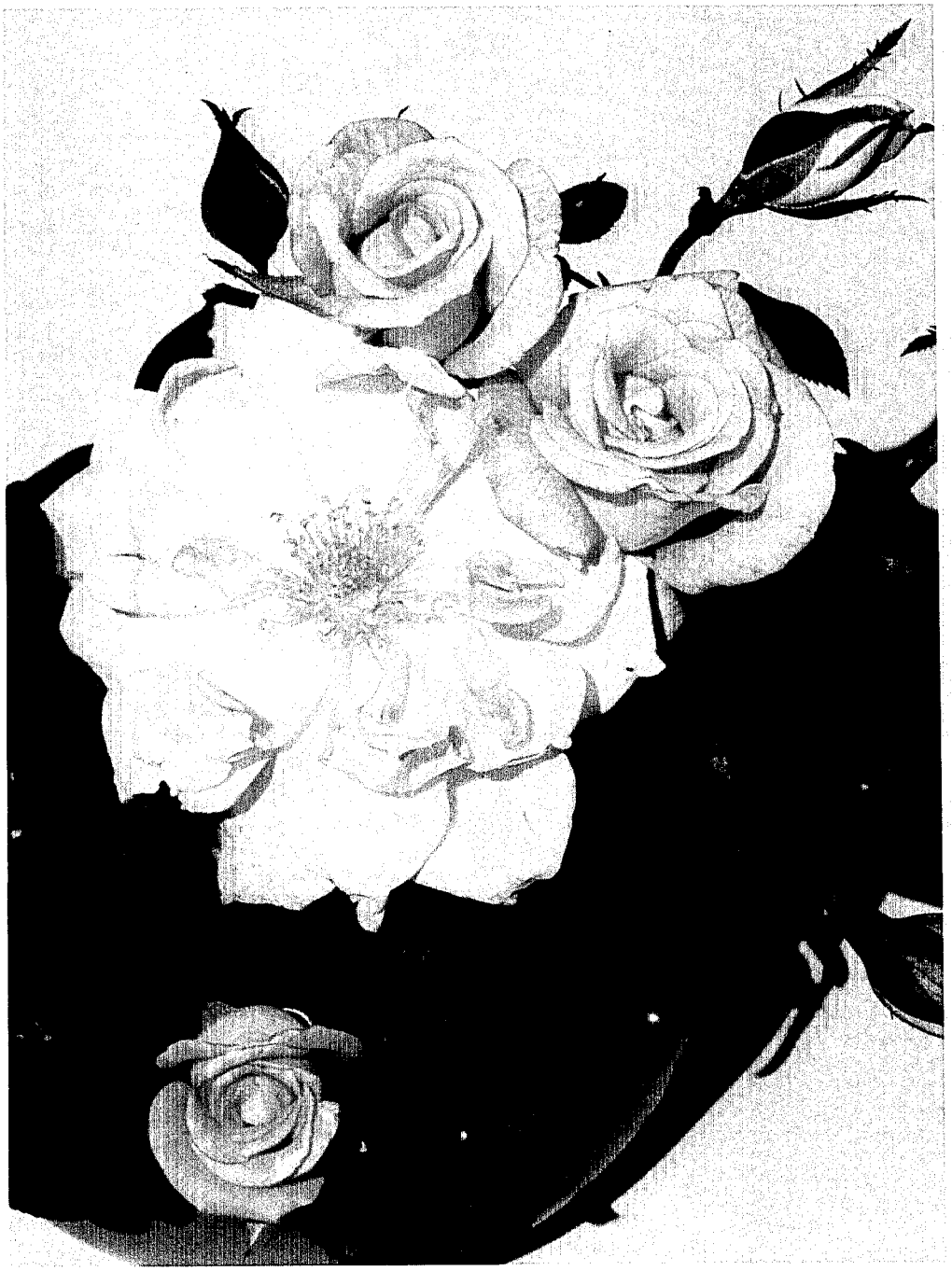

* * * * *